United States Patent
Meulink et al.

(12) 
(10) Patent No.: US 6,514,288 B2
(45) Date of Patent: Feb. 4, 2003

(54) PROSTHETIC STEM WITH STRENGTHENING RIB

(75) Inventors: Steven L. Meulink, Warsaw, IN (US); Jack D. Jennings, Warsaw, IN (US); James L. Crumley, II, Fort Wayne, IN (US); Tracy R. Gilliland, Pierceton, IN (US)

(73) Assignee: Zimmer, Inc., Warsaw, IL (US)

( * ) Notice: Subject to any disclaimer, the term of this patent is extended or adjusted under 35 U.S.C. 154(b) by 22 days.

(21) Appl. No.: 09/792,500

(22) Filed: Feb. 23, 2001

(65) Prior Publication Data

US 2002/0120344 A1 Aug. 29, 2002

(51) Int. Cl.[7] .................................................. A61F 2/32
(52) U.S. Cl. ...................................................... 623/23.3
(58) Field of Search ........................... 623/23.46, 23.15, 623/23.19, 23.2, 23.21, 23.23, 23.24, 23.25, 23.29, 23.3, 23.31, 23.35, 23.36, 23.37, 23.44, 23.45, 23.52, 23.53, 23.54, 23.55, 23.56, 23.57, 23.58, 23.59, 23.6, 23.62

(56) References Cited

U.S. PATENT DOCUMENTS

| | | | | |
|---|---|---|---|---|
| 4,179,485 A | * | 12/1979 | Tritten | 264/628 |
| 4,549,319 A | * | 10/1985 | Meyer | 606/100 |
| 4,623,349 A | * | 11/1986 | Lord | 623/23.44 |
| 4,693,724 A | * | 9/1987 | Rhenter et al. | 623/23.44 |
| 4,718,912 A | | 1/1988 | Crowninshield | 623/23 |
| 4,728,334 A | * | 3/1988 | Spotorno | 623/23.31 |
| 4,728,335 A | * | 3/1988 | Jurgutis | 623/23.23 |
| 4,904,266 A | * | 2/1990 | Barber | 623/23.36 |
| 4,944,761 A | * | 7/1990 | Stuhmer et al. | 623/23.31 |
| 5,222,985 A | * | 6/1993 | Homsy | 623/23.36 |
| 5,246,461 A | * | 9/1993 | Tepic | 623/23.32 |
| 5,336,265 A | | 8/1994 | Serbousek et al. | |
| 5,443,523 A | * | 8/1995 | Mikhail | 623/23.37 |
| 5,504,300 A | * | 4/1996 | Devanathan et al. | 219/121.64 |
| 6,193,761 B1 | * | 2/2001 | Treacy | 433/201.1 |

* cited by examiner

*Primary Examiner*—David J. Isabella
(74) *Attorney, Agent, or Firm*—Baker & Daniels

(57) ABSTRACT

The present invention provides an improved prosthetic stem for implantation in a bone. Specifically, the present invention provides a prosthetic femoral stem having a strengthening rib protruding from the substrate thereof and being flush with a porous coating formed thereon. The strengthening rib is advantageously positioned so as to increase the cross-sectional moment of inertia of the prosthetic femoral stem and thereby decrease the stress on the anterio-lateral surface of the femoral stem. A protrusion in accordance with the present invention may also be utilized with a prosthetic femoral stem absent a porous coating. In such an embodiment, the height of the protrusion is such that the protrusion will be surrounded by the cement mantle formed when the prosthetic femoral component is cemented in a femoral canal.

10 Claims, 2 Drawing Sheets

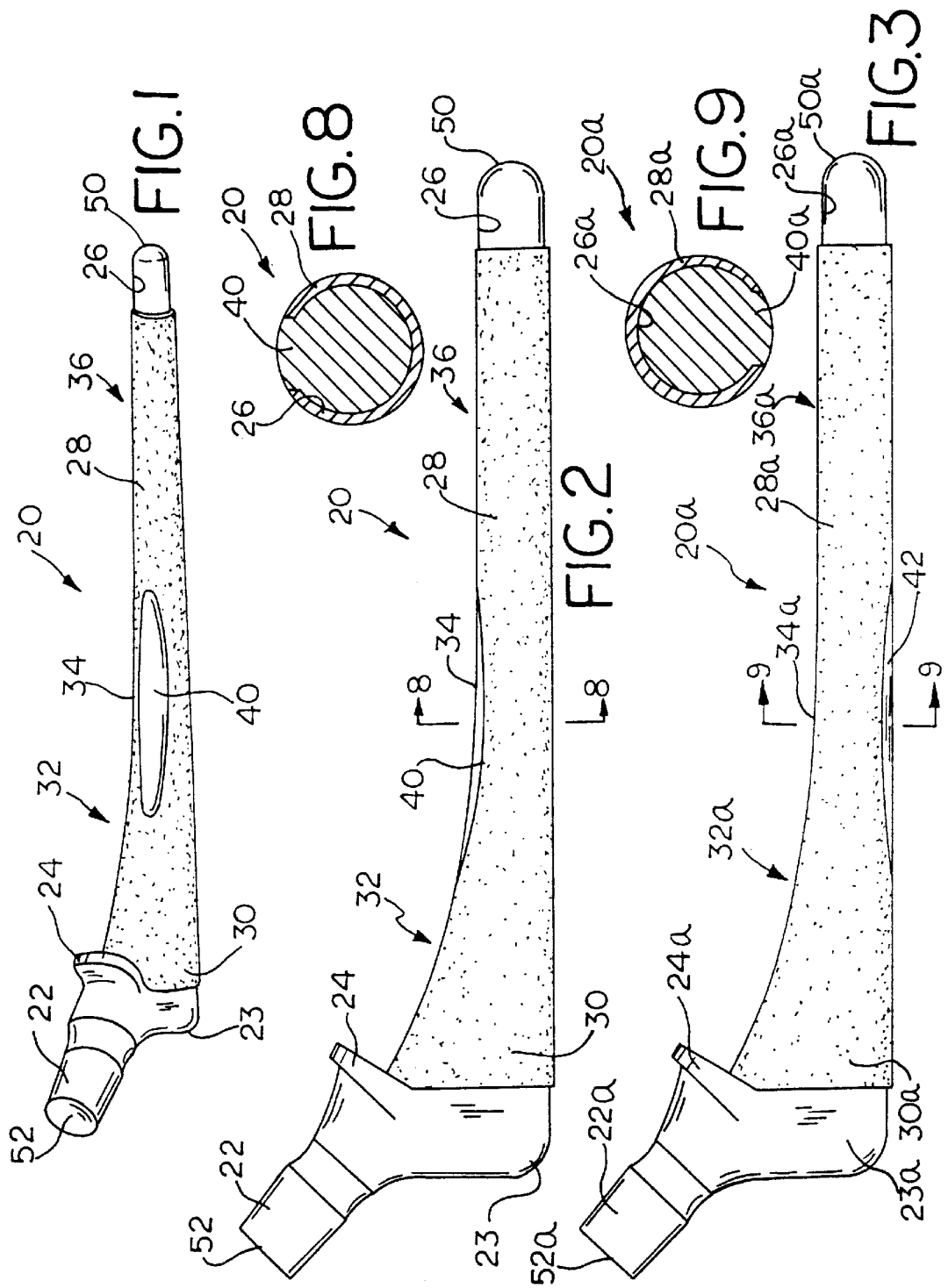

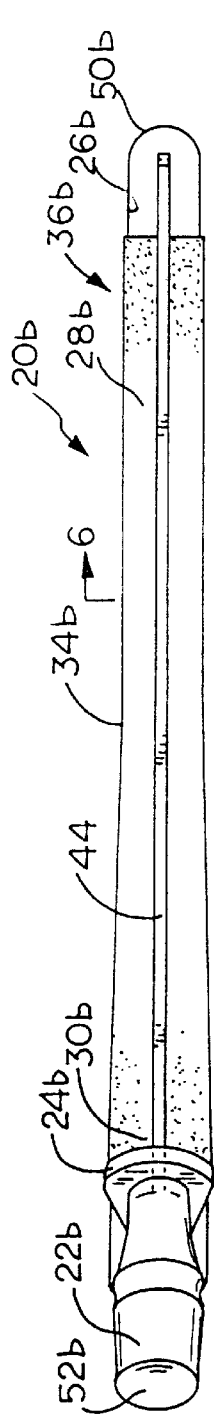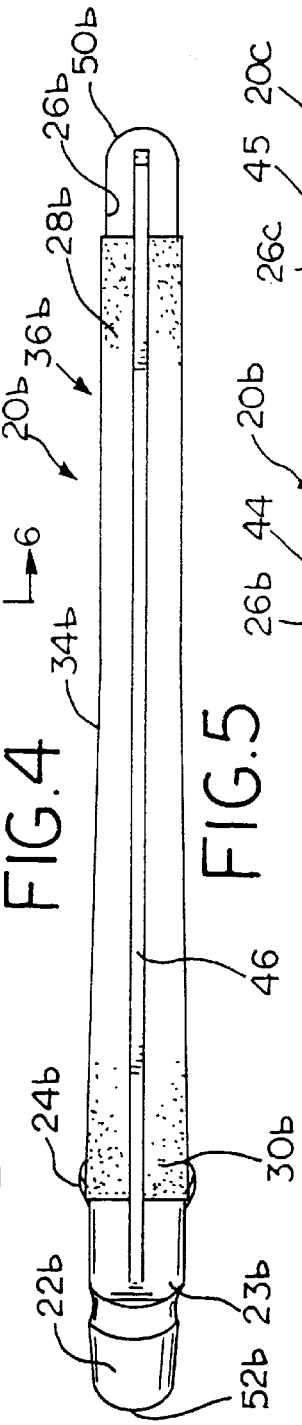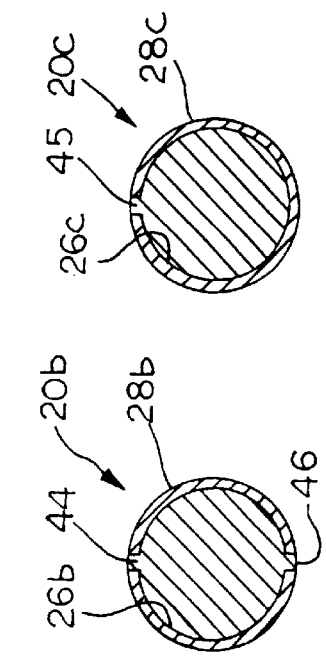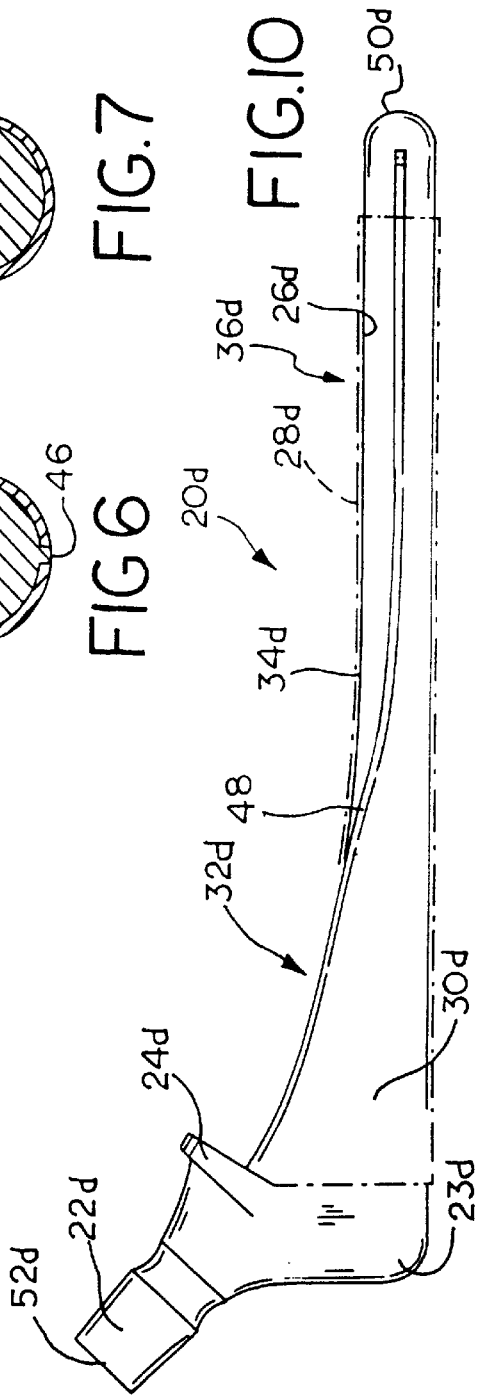

US 6,514,288 B2

PROSTHETIC STEM WITH STRENGTHENING RIB

BACKGROUND OF THE INVENTION

1. Field of the Invention

The present invention relates to a prosthetic stem for implantation in a bone. More particularly, the present invention relates to a prosthetic hip stem (i.e., femoral stem) having a strengthening rib to increase the fatigue strength of the prosthetic stem.

2. Description of the Related Art

Orthopedic implants utilized to replace all, or a portion of, a patient's joint (e.g., the hip) are commonly utilized to restore the use of, or increase the use of a joint which has deteriorated due to, e.g., aging, illness or injury. In the case of hip replacement, femoral components are utilized to replace a portion of the patient's femur including, e.g., the femoral head and neck. A femoral stem is positioned within a canal of the femur and is secured thereto. The femoral stem includes a femoral neck adapted to receive a prosthetic femoral head to complete the femoral prosthesis. Prosthetic femoral stems are generally either cemented in the femoral canal or are interference fit therein.

Femoral stems may advantageously include a porous external surface to accommodate bone ingrowth or cement interdigitation. Various porous substances are utilized to coat the substantially nonporous outer surface (i.e., substrate) of a femoral stem including, e.g., wire mesh, or beaded or dimpled surfaces. For the purposes of this document, "substantially nonporous" signifies a material having less porosity relative to the porous coating of a prosthetic stem.

Femoral stems are susceptible to fatigue failure after repeated loading over time. Stems having a porous coating are generally not as strong as a similarly sized stem absent a porous coating since, e.g., the substantially nonporous core of a coated stem (which is stronger than the porous coating) is smaller than the substantially nonporous core of a similarly sized stem absent porous coating. Furthermore, the porous coating of a femoral stem creates sharp corners between the porous coating and the substrate of the femoral stem. These sharp corners cause stress risers which can weaken the stem.

What is needed in the art is a femoral stem having a structure which increases the fatigue strength of a femoral stem having a porous coating without increasing the external dimensions thereof.

SUMMARY OF THE INVENTION

The present invention provides an improved prosthetic stem for implantation in a bone. Specifically, the present invention provides a prosthetic femoral stem having a strengthening rib protruding from the substrate thereof and being flush with any porous substance formed thereon. The strengthening rib is advantageously positioned so as to increase the cross-sectional moment of inertia of the prosthetic femoral stem and thereby increase the fatigue strength of the prosthetic femoral stem. The strengthening rib of the current invention increases the fatigue strength of the femoral stem not only by increasing the effective core area at a critical area of the stem (i.e., a high stress area where fatigue failure is likely to occur), but also by decreasing the stress risers associated with a porous coating at the aforementioned critical area. The strengthening rib is formed from a substantially nonporous material, and, in one exemplary embodiment is formed from a material substantially identical to the substrate material.

The invention, in one form thereof, comprises a prosthetic stem for implantation in a bone. The prosthetic stem of this form of the current invention includes a neck connected to a shaft, with the neck and shaft forming an obtuse angle. A porous substance protrudes outwardly from a substrate of the prosthetic stem and a substantially nonporous protrusion also protrudes outwardly from the substrate. The substantially nonporous protrusion is substantially flush with the porous substance so that the nonporous protrusion does not increase the external dimensions of the prosthetic stem.

The invention, in another form thereof, comprises a prosthetic hip stem for implantation in a femur utilizing bone cement to form a mantle about the portion of the hip stem inserted into the canal in the femur. The hip stem of this form of the current invention includes a neck connected to a shaft, with the neck extending from a medial side of the hip stem to form an obtuse angle with the shaft. A transition section is positioned intermediate the neck and the shaft and has a transverse cross-sectional area larger than the transverse cross-sectional area of the shaft. A protrusion is positioned on the external surface of the hip stem and has a height whereby the protrusion is covered by the mantle of bone cement when the prosthetic hip stem is implanted in a femur.

The present invention advantageously increases the fatigue strength of a prosthetic femoral stem without increasing the external dimensions thereof.

BRIEF DESCRIPTION OF THE DRAWINGS

The above-mentioned and other features and objects of this invention, and the manner of attaining them, will become more apparent and the invention itself will be better understood by reference to the following description of embodiments of the invention taken in conjunction with the accompanying drawings, wherein:

FIG. 1 is a perspective view of a femoral stem in accordance with the present invention;

FIG. 2 is a side view thereof;

FIG. 3 is a side view of a second embodiment of a femoral stem in accordance with the present invention;

FIG. 4 is a medial view of a third embodiment of a femoral stem in accordance with the present invention FIG. 5 is a lateral view of the femoral stem illustrated in FIG. 4;

FIG. 6 is a cross-sectional view thereof;

FIG. 7 is a cross-sectional view of a fourth embodiment of a femoral stem in accordance with the present invention;

FIG. 8 is a cross-sectional view of the prosthetic femoral stem illustrated in FIG. 2;

FIG. 9 is a cross-sectional view of the prosthetic femoral stem illustrated in FIG. 3; and FIG. 10 is a side view of a fifth embodiment of a prosthetic femoral stem in accordance with the present invention.

Corresponding reference characters indicate corresponding parts throughout the several views. Although the drawings represent embodiments of the present invention, the drawings are not necessarily to scale and certain features may be exaggerated to better illustrate and explain the invention. The exemplifications set out herein illustrate exemplary embodiments of the invention only, and such exemplifications are not to be construed as limiting the scope of the invention in any manner.

DETAILED DESCRIPTION OF THE INVENTION

Referring now to the drawings and particularly to FIG. 1, there is illustrated femoral stem 20 having porous substance 28 affixed to substrate 26 and protrusion 40 extending from substrate 26. As illustrated in FIGS. 2 and 8, protrusion 40 is flush with porous substance 28. The larger effective transverse cross-sectional area of substrate 26 created by protrusion 40 increases the transverse cross-sectional moment of inertia of femoral stem 20 and thereby effects a decrease in stress on the anterio-lateral surface of femoral stem 20. For the purpose of this document, "transverse cross-sectional area" denotes the area of a cross-section taken along a plane substantially perpendicular to the longitudinal axis of femoral shaft 26. Femoral stem 20 generally includes distal end 50, femoral shaft 36, transition section 30 (having medial curve 32), flange 24, shoulder 23, and neck 22 terminating in proximal end 52. The geometry of femoral stem 20 is illustrated by way of example only. It is contemplated that the teachings of the present invention will have applicability to femoral stems of varying geometry.

In the exemplary embodiment of FIGS. 1, 2, and 8, protrusion 40 of femoral stem 20 has a generally oval shape to maximize the coverage of porous substance 28 and minimize the stress concentrations at the edges of protrusion 40. The oval shape of protrusion 40 eliminates sharp corners about the periphery thereof and thereby decreases the stress concentrations at the edges of protrusion 40. The greater transverse cross-sectional area at the midpoint of protrusion 40 is positioned at a critical area of femoral stem 20 (i.e., a high stress area where fatigue failure is likely to occur). The critical area of femoral stem 20 will vary depending upon whether femoral stem is implanted in a right or a left femur. The relatively wide midpoint of protrusion 40 allows femoral stem 20 to accommodate both right and left femur implantations as well as slight rotations of the femoral stem during implantation. Advantageously, protrusion 40 is positioned on the medial side of femoral stem 20 so that protrusion 40 is loaded in compression. In this way, the detrimental effects of stress risers in protrusion 40 are effectively negated.

Femoral stem 20 is, e.g., formed of a cobalt-chromium alloy. However, femoral stem 20 may be constructed of other bio-compatible metals or alloys, such as titanium. Similarly, porous coating 28 comprises, e.g., a beaded coating formed from a cobalt-chromium alloy, although various other porous coatings may be utilized in conjunction with the teachings of the present invention. The generally oval shape of protrusion 40 allows for maximum application of the porous outer surface while providing sufficient material to adequately increase the transverse cross-sectional moment of inertia of femoral stem 20. As stated above, the midpoint of protrusion 40 comprises the portion of protrusion 40 having the greatest transverse cross-sectional area. The midpoint of protrusion 40 is positioned at medial curve tangency 34. Medial curve tangency 34 comprises the portion of medial curve 32 tangent to cylindrical femoral shaft 36. In other words, medial curve tangency 34 is located at the point where medial curve 32 ends and cylindrical femoral shaft 36 begins. In one exemplary femoral stem, medial curve tangency 34 comprises a critical area of the femoral stem (i.e., a high stress area where fatigue failure is likely to occur).

Less protrusion material is required toward the proximal end of the stem because the transverse cross-sectional area of the stem in transition section 30 is larger than the transverse cross-sectional area of femoral shaft 36, while less material is needed toward the distal end of the stem since this end of femoral stem 20 will be solidly fixed in the femur. With this in mind, the transverse cross-sectional area of protrusion 40 of the exemplary embodiment illustrated in FIGS. 1, 2, and 8 generally decreases from the midpoint thereof to the proximal and distal ends thereof to allow for maximum application of the porous coating. In one exemplary embodiment, protrusion 40 extends from it's midpoint approximately 2.5 centimeters (1 inch) into transition section 30 and approximately 2.5 centimeters (1 inch) into femoral shaft 36.

FIGS. 3 and 9 illustrate femoral stem 20a in accordance with a second embodiment of the present invention. The several embodiments of the present invention include similar components to the embodiment illustrated in FIGS. 1, 2, and 8. These similar components are denoted with a reference numeral having a letter appended thereto. For the sake of brevity, these similar components will not all be discussed in conjunction with the various alternative embodiments disclosed herein. Femoral stem 20a includes lateral protrusion 42 of similar shape to medial protrusion 40 illustrated in FIG. 1. Lateral protrusion 42 is positioned on the lateral side of femoral stem 20a with the midpoint thereof generally lying opposite medial curve tangency 34 of femoral stem 20. Various placements of the protrusions of the current invention may be utilized to increase the cross-sectional moment of inertia of the femoral stem and therefore increase the strength of a femoral stem. Furthermore, plural protrusions may be utilized to further increase the strength of a femoral component in accordance with the present invention. For example, medial protrusion 40 (FIG. 1) may be used in conjunction with lateral protrusion 42 (FIG. 3) to form a femoral stem in accordance with the present invention.

FIGS. 4–6 illustrate a third embodiment of the present invention having medial rib 44 and lateral rib 46. As illustrated in FIG. 6, medial rib 44 and lateral rib 46 extend from substrate 26b and are flush with porous coating 28b. Ribs 44, 46 run substantially the length of femoral stem 20b and include end points which gradually taper to transition into substrate 26b. The smooth transitions provided by the tapering of the end points of ribs 44, 46 function to decrease stress risers therein. As illustrated in FIG. 4, medial rib 44 generally runs from distal end 50b to the distal side of flange 24b. Similarly, lateral rib 46 runs from distal end 50b to shoulder 23b. Although illustrated as running substantially the length of femoral stem 20b, ribs 44, 46 may be partial ribs running along only a portion of the length of femoral stem 20b. It is further contemplated that ribs 44, 46 could be of varying width, with the greatest transverse cross-sectional area (associated with the greatest width) being positioned at a critical area.

FIG. 7 illustrates a cross-sectional view of femoral stem 20c having a single rib 45. Rib 45 may be either a medial or lateral rib as discussed above with respect to femoral stem 20b. FIG. 7 is provided to illustrate a single rib configuration in accordance with the present invention, as opposed to the dual rib configuration of FIGS. 4–6.

FIG. 10 illustrates femoral stem 20d having helical rib 48. Helical rib 48 includes a proximal end adjacent the distal side of flange 50d and a distal end adjacent distal end 50d of femoral stem 20d. The proximal end of helical rib 48 is rotated 90° from the distal end of helical rib 48. Helical rib 48 will have particular applicability to longer femoral stems which experience substantial bending in the anterior-posterior plane of the distal portions thereof. The helical arrangement of rib 48 allows for rib placement in both the medial-lateral plane and the anterior-posterior plane of femoral stem 20d, with the anterior-posterior placement of rib 48 advantageously occurring in the distal portion of the femoral stem.

While described above with respect to a femoral stem having a porous coating, the ribs of the current invention may be utilized with a femoral stem absent such a porous outer coating. In such applications, the protrusions of the present invention will extend outwardly from the external surface of the femoral stem. In such situations, the height of the ribs will be sized so that the protrusion will be covered by the cement mantle formed by the bone cement utilized to implant the femoral stem.

While this invention has been described as having exemplary designs, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A prosthetic stem for implantation in a bone, the prosthetic stem having a substrate, the prosthetic stem comprising:
   a shaft;
   a neck connected to said shaft, said neck and said shaft forming an obtuse angle;
   a porous substance protruding outwardly from the substrate of the prosthetic stem; and
   a substantially nonporous protrusion protruding outwardly from the substrate of the prosthetic stem, said substantially nonporous protrusion substantially flush with said porous substance, said protrusion defining a periphery, said porous substance encircling said periphery of said protrusion.

2. A prosthetic stem for implantation in a bone, the prosthetic stem having a substrate, the prosthetic stem comprising:
   a shaft;
   a neck connected to said shaft, said neck and said shaft forming an obtuse angle;
   a porous substance protruding outwardly from the substrate of the prosthetic stem; and
   a substantially nonporous protrusion protruding outwardly from the substrate of the prosthetic stem, said substantially nonporous protrusion substantially flush with said porous substance, said protrusion forming a generally helical pattern along the prosthetic stem, said protrusion having a distal and a proximal end, said distal end rotated ninety degrees from said proximal end.

3. The prosthetic hip stem of claim 4, further comprising a second substantially nonporous protrusion protruding outwardly from the substrate of the prosthetic hip stem, said second substantially nonporous protrusion substantially flush with said porous substance, said second substantially nonporous protrusion positioned on a lateral side of said hip stem.

4. A prosthetic hip stem for implantation in a femur, the prosthetic hip stem having a substrate, the prosthetic hip stem comprising:
   a shaft having a medial side;
   a neck connected to said shaft, said neck extending from said medial side of said hip stem, said neck and said shaft forming an obtuse angle;
   a porous substance protruding outwardly from the substrate of the prosthetic hip stem;
   a first substantially nonporous protrusion protruding outwardly from the substrate of the prosthetic hip stem, said first substantially nonporous protrusion substantially flush with said porous substance; and
   a transition section intermediate said neck and said shaft, said transition section defining a medial curve and a medial curve tangency, said first substantially nonporous protrusion having a length, said first substantially nonporous protrusion having a variable cross-section along said length, said substantially nonporous protrusion having a maximum transverse cross-section positioned adjacent said medial curve tangency.

5. A prosthetic hip stem for implantation in a femur, the prosthetic hip stem having a substrate, the prosthetic hip stem comprising:
   a shaft having a medial side;
   a neck connected to said shaft, said neck extending from said medial side of said hip stem, said neck and said shaft forming an obtuse angle;
   a porous substance protruding outwardly from the substrate of the prosthetic hip stem; and
   a first substantially nonporous protrusion protruding outwardly from the substrate of the prosthetic hip stem, said first substantially nonporous protrusion substantially flush with said porous substance, said first substantially nonporous protrusion having a length and a midpoint along said length, said first substantially nonporous protrusion having a variable transverse cross-section along said length, said variable transverse cross-section defining a maximum transverse cross-section at said midpoint.

6. A prosthetic hip stem for implantation in a femur utilizing bone cement to form a mantle about a portion of the hip stem inserted into a canal in the femur, the prosthetic hip stem having an external surface, the prosthetic hip stem comprising:
   a shaft having a medial side;
   a neck connected to said shaft, said neck extending from said medial side of said hip stem, said neck and said shaft forming an obtuse angle;
   a first protrusion protruding outwardly from the external surface of the prosthetic hip stem, said first protrusion having a height whereby said first protrusion is covered by the mantle, said first protrusion having a length and a midpoint along said length, said first protrusion having a variable transverse cross-section along said length, said variable transverse cross-section defining a maximum transverse cross-section at said midpoint.

7. The prosthetic hip stem of claim 6, further comprising a second protrusion protruding outwardly from the external surface of the prosthetic hip stem, said second protrusion having a height whereby said second protrusion is covered by the mantle, said second protrusion positioned on a lateral side of said hip stem.

8. A prosthetic hip stem for implantation in a femur utilizing bone cement to form a mantle about a portion of the hip stem inserted into a canal in the femur, the prosthetic hip stem having an external surface, the prosthetic hip stem comprising:

a shaft having a medial side;

a neck connected to said shaft, said neck extending from said medial side of said hip stem, said neck and said shaft forming an obtuse angle;

a first protrusion protruding outwardly from the external surface of the prosthetic hip stem, said first protrusion having a height whereby said first protrusion is covered by the mantle, said first protrusion forming a generally helical pattern along the prosthetic hip stem, said first protrusion having a distal and a proximal end, said distal end rotated ninety degrees from said proximal end.

9. A prosthetic stem for implantation in a bone, the prosthetic stem having a substrate, the prosthetic stem comprising:

a shaft;

a neck connected to said shaft, said neck and said shaft forming an obtuse angle;

a porous substance protruding outwardly from the substrate of the prosthetic stem;

a substantially nonporous protrusion protruding outwardly from the substrate of the prosthetic stem, said substantially nonporous protrusion substantially flush with said porous substance, said substantially nonporous protrusion having a length and a midpoint along said length, said substantially nonporous protrusion having a variable transverse cross-section along said length, said variable transverse cross-section defining a maximum transverse cross-section at said midpoint.

10. A prosthetic stem for implantation in a bone, the prosthetic stem having a substrate, the prosthetic stem comprising:

a shaft;

a neck connected to said shaft, said neck and said shaft forming an obtuse angle;

a porous substance protruding outwardly from the substrate of the prosthetic stem;

a substantially nonporous protrusion protruding outwardly from the substrate of the prosthetic stem, said substantially nonporous protrusion substantially flush with said porous substance;

a transition section intermediate said neck and said shaft, said transition section defining a medial curve and a medial curve tangency, said substantially non porous protrusion having a length, said substantially nonporous protrusion having a variable cross-section along said length, said substantially nonporous protrusion defining a maximum transverse cross-section adjacent said medial curve tangency.

* * * * *